(12) United States Patent
Shan et al.

(10) Patent No.: US 8,524,949 B2
(45) Date of Patent: Sep. 3, 2013

(54) AGOMELATINE HYDROHALIDE COMPLEX AND PREPARATION METHOD THEREOF

(75) Inventors: Hanbin Shan, Gaoan (CN); Peng Zhang, Pudong New Area (CN); Zhedong Yuan, Shanghai (CN); Xudong Jiang, Jing'an District (CN); Yu Huang, Jing'an District (CN); Hubo Wang, Minhang District (CN); Xufeng Cao, Xixia District (CN); Xingdong Cheng, Daiyue District (CN); Hongjuan Pan, Shanghai (CN); Xiong Yu, Hongkou District (CN)

(73) Assignee: Les Laboratories Servier, Suresnes Cedex (FR)

( * ) Notice: Subject to any disclaimer, the term of this patent is extended or adjusted under 35 U.S.C. 154(b) by 202 days.

(21) Appl. No.: 13/138,511

(22) PCT Filed: Feb. 26, 2010

(86) PCT No.: PCT/CN2010/070780
§ 371 (c)(1),
(2), (4) Date: Aug. 26, 2011

(87) PCT Pub. No.: WO2010/097052
PCT Pub. Date: Sep. 2, 2010

(65) Prior Publication Data
US 2011/0313198 A1    Dec. 22, 2011

(30) Foreign Application Priority Data

Feb. 27, 2009   (CN) .......................... 2009 1 0046782

(51) Int. Cl.
*C07C 233/05*  (2006.01)
(52) U.S. Cl.
USPC .......................................... 564/172
(58) Field of Classification Search
USPC .......................................... 564/172
See application file for complete search history.

(56) References Cited

U.S. PATENT DOCUMENTS

2005/0182275 A1    8/2005  Stolting

FOREIGN PATENT DOCUMENTS

| CA | 2495967 | * | 8/2005 |
| CN | 101041629 | | 9/2007 |

OTHER PUBLICATIONS

International Preliminary Report on Patentability for PCT/CN2010/070780, 2010.
International Search Report for PCT/CN2010/070780 of May 4, 2010.

* cited by examiner

*Primary Examiner* — Shailendra Kumar
(74) *Attorney, Agent, or Firm* — Hueschen and Sage

(57) ABSTRACT

The present invention relates to a complex of agomelatine and to preparation thereof. The hydrogen halide complex of agomelatine obtained through the present method is more soluble, more stable, and of higher purity than agomelatine itself, making it more suitable to be used in pharmaceutical preparation. Using this method, product of high purity can be obtained through a simple process, without having to incur further complicated steps.

6 Claims, No Drawings

AGOMELATINE HYDROHALIDE COMPLEX AND PREPARATION METHOD THEREOF

This application is a 371 of PCT/CN2010/070780, filed Feb. 26, 2010.

TECHNICAL FIELD

The present invention relates to a complex of agomelatine and to preparation thereof.

TECHNICAL BACKGROUND

The structure of agomelatine (1), with the chemical name N-[2-(7-methoxy-1-naphthyl)ethyl]-acetamide, is shown by the formula II below. It is marketed under the trademark name of Valdoxan by the French company Servier as a melatonin agonist and antagonist of the 5HT2C receptor, for the treatment of depression, sleep enhancement and maintenance of sexual function.

(II)

In view of its pharmaceutical value, it is important then to be able to produce the compound or a complex thereof with better purity, solubility and more reproducible performance.

SUMMARY OF THE INVENTION

The objective of the present invention is to provide a hydrogen halide complex of agomelatine, which is more soluble, more stable, and of higher purity, making it more suitable to be used in pharmaceutical preparations containing agomelatine. A further objective of the present invention is to provide a preparation method for the said hydrogen halide complex of agomelatine.

When the present inventors attempted to purify agomelatine product, they surprisingly found that agomelatine can form a physically and chemically stable complex when mixed with inorganic acids such as hydrochloric acid (HCl), hydrobromic acid (HBr), and hydroiodic acid (HI). The said complex is suitable for the preparation of pharmaceutical compositions. However, when other conventional inorganic acids (such as sulphuric acid, phosphoric acid, perchloric acid) or organic acids (such as acetic acid, oxalic acid, tartaric acid, fumaric acid) were used, it was not easy to produce the complex.

The said hydrogen halide complex of agomelatine has the following structure:

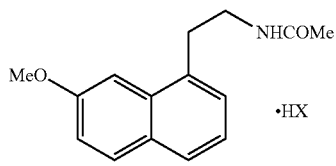

wherein X is halogen, preferably Cl or Br.

The present invention provides a preparation method for the said hydrogen halide complex of agomelatine, wherein agomelatine is reacted with HX in any form to produce the complex. In the process, agomelatine can be dissolved in an organic solvent before HX is bubbled in and the precipitated crystal is rinsed and dried; alternatively, agomelatine can be added to an organic solution containing HX and the precipitated crystal is rinsed and dried. The concentration of HX should be the minimal required for precipitation of the complex. The results from many experiments showed that HCl in ethyl acetate (HCl/EtOAc) produces the complex with the highest yield. Therefore, the most preferred method is to add agomelatine to the solution of HCl in EtOAc to allow the target product to crystallise, which is then rinsed and dried.

In the present method of preparing hydrogen halide complexes of agomelatine, there is no restriction on the organic solvent used as long as it is able to dissolve the reactants, agomelatine and HX, and allows the precipitation of the complex. The said solvent may be selected from ethyl acetate, methyl acetate, n-butyl acetate, acetone, acetonitrile and the like, ethyl acetate being the most preferred. However, low-polarity solvents such as alcohols (ethanol and methanol etc.), DMF, DMSO are not suitable.

BENEFITS OF THIS INVENTION

The present invention is advantageous in that the inventors found that among so many conventional acids, agomelatine can only react with hydrogen halide to form a stable complex, the physical properties of which, such as stability, solubility, and hygroscopicity, are better than those products of agomelatine with any other acid. The process is also less complicated than if other acids were used.

The hydrogen halide complex of agomelatine produced according to the present method is more soluble, more stable, and of higher purity than agomelatine itself, making it more suitable to be used in pharmaceutical preparations. In addition, a product of high purity can be obtained through a simple process, without having to incur further complicated steps.

CONTENT OF THE INVENTION

The following examples are designed to further illustrate the present invention, wherein the specific parameters and steps are not intended to limit the required scope of protection of the present invention.

Example 1

1.0 g of agomelatine was dissolved in 10 ml of EtOAc with stirring, dry HCl gas was bubbled through the solution slowly at room temperature until the solution stopped gaining weight. The mixture was then filtered, the solid washed twice with 2 ml of EtOAc and dried at 30° C. to yield 1.05 g of white solid (purity: 99.7%).

Analytical results: ($C_{15}H_{17}NO_2$.HCl)
Calculated: Cl % (12.69%)
Found: Cl % (12.44%)
Melting point: 64-66° C.

Example 2

3.0 g of agomelatine was dissolved in 30 ml of EtOAc with stirring, dry HCl gas was bubbled through the solution at room temperature until the solution stopped gaining weight.

The mixture was then filtered, the solid washed twice with 5 ml of EtOAc and dried at 30° C. to yield 3.2 g of white solid (purity: 99.8%).

Analytical results: ($C_{15}H_{17}NO_2 \cdot HCl$)
Calculated: Cl % (12.69%)
Found: Cl % (12.60%)
Melting point: 64-66° C.

Example 3

10 g of agomelatine was dissolved in 100 ml of EtOAc with stirring, dry HCl gas was bubbled through the solution at room temperature until the solution stopped gaining weight. The mixture was then filtered, the solid washed twice with 10 ml of EtOAc and dried at 30° C. to yield 10.8 g of white solid (purity: 99.8%).

Analytical results: ($C_{15}H_{17}NO_2 \cdot HCl$)
Calculated: Cl % (12.69%)
Found: Cl % (12.21%)
Melting point: 64-66° C.

Example 4

10 g of agomelatine was added to 100 ml of EtOAc solution saturated with HCl gas. The mixture was stirred for 1 h at room temperature and then filtered, the solid washed twice with 10 ml of EtOAc and dried at 30° C. to yield 10.9 g of white solid (purity: 99.8%).

Analytical results: ($C_{15}H_{17}NO_2 \cdot HCl$)
Calculated: Cl % (12.69%)
Found: Cl % (12.39%)
Melting point: 64-66° C.

Example 5

According to the method for preparing agomelatine disclosed in Chinese Patent CN1680284A, a solution of 17.3 g of 2-(7-methoxy-1-naphthyl)ethylamine hydrochloride and 6.6 g sodium acetate in ethanol was added to a reactor, then 7.9 g of acetic anhydride was added with stirring. The mixture was heated to reflux and then 60 ml of water was added. The mixture was cooled down to room temperature and the solid was filtered off. The filtrate was extracted three times with 20 ml of EtOAc and the combined extracts were evaporated to dryness. The obtained solid was then dissolved in 100 ml of EtOAc with stirring; dry HCl gas was bubbled through the solution at room temperature until the solution stopped gaining weight. The mixture was then filtered, the solid washed twice with 10 ml of EtOAc and dried at 30° C. to yield 18.5 g of white solid (yield: 91%; purity: 99.1%).

Analytical results: ($C_{15}H_{17}NO_2 \cdot HCl$)
Calculated: Cl % (12.69%)
Found: Cl % (12.57%)
Melting point: 64-66° C.

Example 6

According to the method for preparing agomelatine disclosed in Chinese Patent CN1680284A, a solution of 17.3 g of 2-(7-methoxy-1-naphthyl)ethylamine hydrochloride and 6.6 g sodium acetate in ethanol was added to a reactor, then 7.9 g of acetic anhydride was added with stirring. The mixture was heated to reflux and then 60 ml of water was added. The mixture was cooled down to room temperature and the solid was filtered off. The filtrate was extracted three times with 20 ml of EtOAc and the combined extracts were evaporated to dryness. The obtained solid was then added to 100 ml of EtOAc solution saturated with HCl gas and stirred for 1 h at room temperature. The mixture was then filtered, the solid washed twice with 10 ml of EtOAc and dried at 30° C. to yield 18.7 g of white solid (yield: 92%; purity: 99.8%).

Analytical results: ($C_{15}H_{17}NO_2 \cdot HCl$)
Calculated: Cl % (12.69%)
Found: Cl % (12.70%)
Melting point: 64-66° C.

Example 7

10 g of agomelatine was dissolved in 100 ml of EtOAc with stirring, and dry HBr gas was bubbled through the solution at room temperature until it stopped gaining weight. The mixture was then filtered, the solid washed twice with 10 ml of EtOAc and dried at 30° C. to yield 11.2 g of white solid (purity: 99.3%).

Analytical results: ($C_{15}H_{17}NO_2 \cdot HCl$)
Calculated: Br % (24.6%)
Found: Br % (23.8%)
Melting point: 85-87° C.

Example 8

1 g of agomelatine was dissolved in 10 ml of EtOAc with stirring, and concentrated $H_2SO_4$ was added dropwise at room temperature. No solid precipitated during the entire process.

Example 9

1 g of agomelatine was dissolved in 10 ml of EtOAc with stirring, and concentrated $H_2SO_4$ was added dropwise at −10° C. No solid precipitated during the entire process.

Example 10

1 g of agomelatine was dissolved in 10 ml of EtOAc with stirring, and glacial acetic acid was added dropwise at −10° C. No solid precipitated during the entire process.

Example 11

1 g of agomelatine was dissolved in 10 ml of EtOAc with stirring, and fumaric acid was added dropwise at −10° C. No solid precipitated during the entire process.

Detection Method

The complex of agomelatine with HCl and HBr were both placed in an incubator at 40° C. for 30 days. Afterwards, the stability of these crystals was studied using HPLC.

1. Purity Determination

HPLC conditions: C18 column; mobile phase: 10 mM/L phosphate buffer (adjusted to pH 7.0 with NaOH): acetonitrile=2:7 (v/v); column temperature: 40° C.; detection wavelength: 220 nm; the internal standard method was used.

The products were each dissolved in the mobile phase at 1 mg/mL. 10 μL was injected into the chromatograph and chromatograms were recorded.

2. Content Determination

The same method was used for the purity test, except that an external standard was used. The results are shown in the table below:

TABLE 1

| Agomelatine Complex | Day 0 | Day 5 | Day 10 | Day 30 |
|---|---|---|---|---|
| Agomelatine•HCl | 99.8% | 99.8% | 99.8% | 99.8% |
| Agomelatine•HBr | 99.3% | 99.3% | 99.3% | 99.3% |

3. Water Solubility

HPLC with external standard was used in the analysis. The results are shown below.

TABLE 2

| | Sample | | |
|---|---|---|---|
| | Agomelatine | Agomelatine•HBr | Agomelatine•HCl |
| Purity | 99.79% | 99.77% | 99.82% |
| Solubility (mg/ml) | 1.11 | 2.14 | 1.60 |

The invention claimed is:

1. A hydrogen halide complex of agomelatine, which has the following structure:

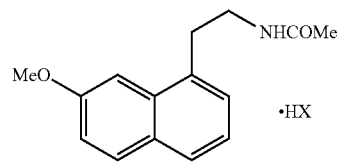

wherein X represents halogen.

2. The hydrogen halide complex of agomelatine according to claim 1, wherein X represents Cl or Br.

3. A method for the preparation of the hydrogen halide complex of agomelatine according to claim 1, wherein agomelatine is reacted with HX in any form to produce the complex.

4. The method for the preparation of the hydrogen halide complex of agomelatine according to claim 3, wherein agomelatine is dissolved in an organic solvent, HX gas is bubbled through the resulting solution, and the resulting crystal is precipitated.

5. The method for the preparation of the hydrogen halide complex of agomelatine according to claim 3, wherein agomelatine is added to an organic solution containing HX and the resulting crystal is precipitated.

6. The method for the preparation of the hydrogen halide complex of agomelatine according to claim 4, wherein HX gas is bubbled through the solution until the solution is saturated.

* * * * *

UNITED STATES PATENT AND TRADEMARK OFFICE
CERTIFICATE OF CORRECTION

PATENT NO.        : 8,524,949 B2
APPLICATION NO.   : 13/138511
DATED             : September 3, 2013
INVENTOR(S)       : Shan et al.

Page 1 of 1

It is certified that error appears in the above-identified patent and that said Letters Patent is hereby corrected as shown below:

On the Title Page, item [73]: "Les Laboratories Servier" should be
--Les Laboratoires Servier--.

On the Title Page, item [56]: "2005/0182275" should be
--2005/0182276--.

Signed and Sealed this
Fifteenth Day of October, 2013

Teresa Stanek Rea
*Deputy Director of the United States Patent and Trademark Office*